United States Patent
Chung et al.

(10) Patent No.: US 9,145,348 B2
(45) Date of Patent: Sep. 29, 2015

(54) PROCESS FOR SYNTHESIZING A CETP INHIBITOR

(71) Applicant: Merck Sharp & Dohme Corp., Rahway, NJ (US)

(72) Inventors: Cheol K. Chung, Westfield, NJ (US); Guy R. Humphrey, Hillsborough, NJ (US); Peter E. Maligres, Fanwood, NJ (US); Timothy J. Wright, Scotch Plains, NJ (US)

(73) Assignee: Merck Sharpe & Dohme Corp., Rahway, NJ (US)

( * ) Notice: Subject to any disclaimer, the term of this patent is extended or adjusted under 35 U.S.C. 154(b) by 0 days.

(21) Appl. No.: 14/355,105

(22) PCT Filed: Oct. 26, 2012

(86) PCT No.: PCT/US2012/062243
§ 371 (c)(1),
(2) Date: Apr. 29, 2014

(87) PCT Pub. No.: WO2013/066768
PCT Pub. Date: May 10, 2013

(65) Prior Publication Data
US 2014/0303380 A1    Oct. 9, 2014

Related U.S. Application Data

(60) Provisional application No. 61/553,515, filed on Oct. 31, 2011.

(51) Int. Cl.
| | |
|---|---|
| *C07D 263/20* | (2006.01) |
| *C07C 41/18* | (2006.01) |
| *C07C 41/30* | (2006.01) |
| *A01N 43/76* | (2006.01) |
| *A61K 31/421* | (2006.01) |

(52) U.S. Cl.
CPC ............... *C07C 41/18* (2013.01); *C07C 41/30* (2013.01); *C07D 263/20* (2013.01)

(58) Field of Classification Search
CPC ...... A01N 43/76; A61K 31/421; C07C 41/18; C07D 263/20
See application file for complete search history.

(56) References Cited

U.S. PATENT DOCUMENTS

| | | | |
|---|---|---|---|
| 7,781,426 B2 * | 8/2010 | Ali et al. | 514/217.1 |
| 7,863,307 B2 | 1/2011 | Miller et al. | |
| 8,242,145 B2 * | 8/2012 | Hutchinson et al. | 514/351 |
| 2004/0127574 A1 * | 7/2004 | Kori et al. | 514/651 |
| 2006/0040999 A1 | 2/2006 | Ali et al. | |
| 2008/0242711 A1 | 10/2008 | Tung | |
| 2009/0042892 A1 | 2/2009 | Ali et al. | |
| 2009/0127548 A1 * | 5/2009 | Inoue et al. | 257/43 |
| 2011/0178199 A1 | 7/2011 | Enomura | |
| 2014/0135368 A1 * | 5/2014 | Humljan et al. | 514/376 |

FOREIGN PATENT DOCUMENTS

| | | | |
|---|---|---|---|
| WO | WO 2006014357 A1 * | 2/2006 | |
| WO | WO2007005572 A1 | 1/2007 | |
| WO | WO 2008082567 A1 * | 7/2008 | |

OTHER PUBLICATIONS

Tet. Lett. 1990, 31(21), 3031-3034.*
Tet. Lett. 2007, 48, 4825-4829.*
J. Med. Chem. 2011, 54(13), 4880-4895.*
International Search Report for PCT/US2012/62243 mailed on Oct. 26, 2012 12 pages.

* cited by examiner

*Primary Examiner* — Joseph Kosack
*Assistant Examiner* — Amanda L Aguirre
(74) *Attorney, Agent, or Firm* — Eric A. Meade; Catherine D. Fitch

(57) ABSTRACT

An efficient process is disclosed for producing the compound of formula I, which is the CETP inhibitor anacetrapib, which raises HDL-cholesterol and reduces LDL-cholesterol in human patients and may be effective for treating or reducing the risk of developing atherosclerosis:

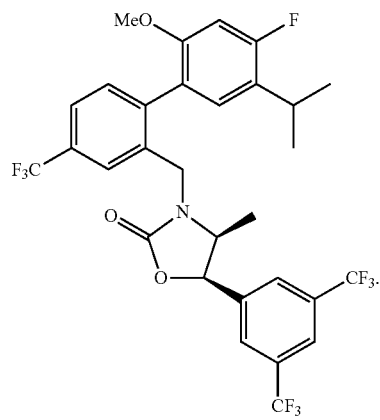

11 Claims, No Drawings

PROCESS FOR SYNTHESIZING A CETP INHIBITOR

CROSS REFERENCE TO RELATED APPLICATIONS

This application is a U.S. National Phase application under 35 U.S.C. §371 of International Application No. PCT/US12/62243, filed Oct. 26, 2012, which claims the benefit of U.S. Provisional Application No. 61/553,515, filed Oct. 31, 2011. Each of the aforementioned applications is hereby incorporated by reference in its entirety.

FIELD OF THE INVENTION

This invention relates to an efficient process for synthesizing a CETP inhibitor and key chemical intermediates in the process. The product of the process is the CETP inhibitor anacetrapib, which raises HDL-cholesterol and lowers LDL-cholesterol in human patients, and may have utility in treating, preventing, or delaying the onset of atherosclerosis or slowing its progression.

BACKGROUND OF THE INVENTION

Atherosclerosis and its clinical consequences, coronary heart disease (CHD), stroke and peripheral vascular disease, represent an enormous burden on the health care systems of the industrialized world. In the United States alone, greater than one half million deaths are attributed to CHD each year. This toll is expected to grow as the average age of the population increases and as an epidemic in obesity and diabetes continues to grow.

Inhibition of CETP is a promising but unproven approach to reducing the incidence of atherosclerosis. Statins have reduced the incidence of CHD by reducing LDL-cholesterol (the "bad cholesterol"), but are relatively ineffective at raising HDL-cholesterol ("the good cholesterol"). CETP inhibitors raise HDL-cholesterol, and may provide a potent new tool for reducing CHD and atherosclerosis in the general population. Torcetrapib was the first CETP inhibitor to be tested in human patients. The pivotal clinical trial of torcetrapib, an outcomes study, was terminated early because of higher mortality in the test group of patients who were taking the drug concomitantly with a statin compared with a group of patients who were taking a placebo and a statin. Subsequent research has suggested that the higher mortality in the test group was caused by off-target activity and was not related to CETP inhibition. Two newer drugs, anacetrapib and dalcetrapib, have also been in Phase III outcomes trials. The dalcetrapib trial was terminated early because an interim review found that there was no clinical benefit to the patients who were taking dalcetrapib, but that there were also no safety issues with the drug. Anacetrapib is currently being studied in an outcomes trial which will not be completed until about 2017. Data from an earlier non-outcomes trial of anacetrapib indicated that anacetrapib is unlikely to have the same kinds of safety issues that were observed with torcetrapib.

A process for making anacetrapib was previously disclosed in a published patent application (WO 2007/005572).

SUMMARY OF THE INVENTION

An improved process is provided herein for manufacturing anacetrapib and key intermediates in its manufacture. Anacetrapib is shown below as the compound having Formula I:

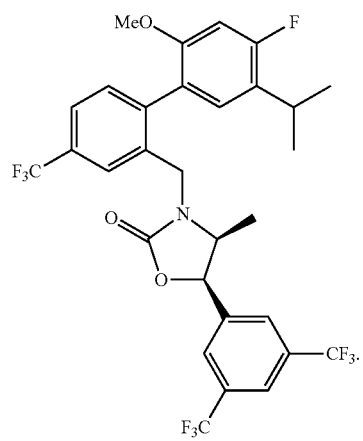

The final step in both processes is the alkylation reaction of an oxazolidinone compound of formula III wherein Ar is 3,5-bis(trifluoromethyl)phenyl with the biaryl chloride of Formula II yielding anacetrapib. The final step described herein uses a milder base than was used in WO 2007/005572.

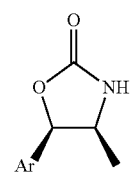

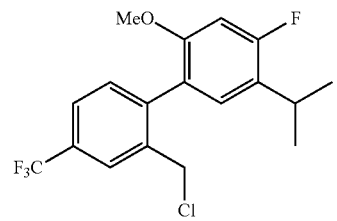

The process disclosed herein provides a more streamlined and economical process for making anacetrapib and the intermediate biaryl compound of formula II than was disclosed in WO 2007/005572. The process is more environmentally friendly ("greener") than the process that was disclosed in WO 2007/005572 for making anacetrapib. The process described herein is more efficient in terms of energy use, reduction of solid waste products, control of impurities, higher chemical yields, and the reduced use of corrosive reagents. This process also eliminates a difficult step that requires cryogenic conditions. Finally, the mild alkylation conditions disclosed for the last step minimize or eliminate epimerization at the stereogenic centers which are present in the oxazolidinone compound (III), thereby leading to improved yields and purer products.

DETAILED DESCRIPTION OF THE INVENTION

A schematic description of the process is shown in the Scheme below:

Scheme

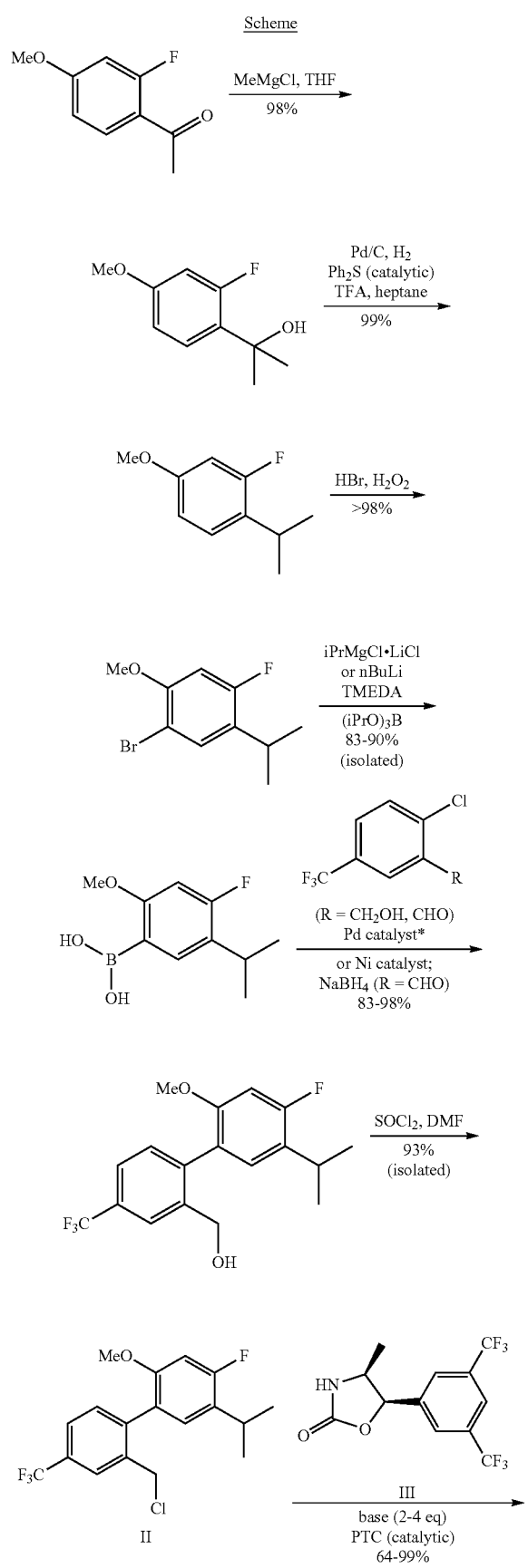

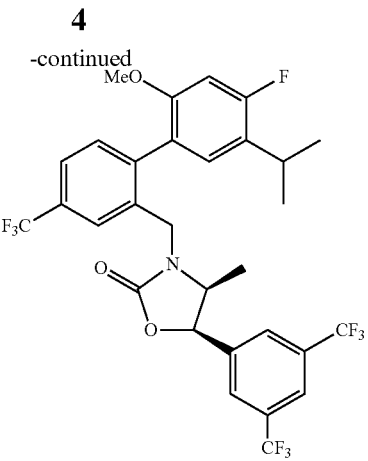

*catalysts for Coupling Reaction

The final step in the process for making compound I is the alkylation of oxazolidinone III with biaryl chloride II in the presence of a phase transfer catalyst, a base, and a solvent suitable for phase transfer catalysis.

The phase-transfer catalyst used in the alkylation reaction may be a tetraalkylammonium halide, a crown ether, or a quaternary phosphonium halide, where the halides are chloride, bromide, or iodide, wherein the 4 groups attached to the P in the quaternary phosphonium halides can be alkyl, aryl, or mixtures thereof, and wherein the alkyl groups in the ammonium and phosphonium halides can be $C_1$-$C_{20}$, but preferably are $C_1$-$C_4$. Examples of phase transfer catalysts as described above include, but are not limited to, tetrabutylammonium chloride, tetrabutylammonium bromide, tetrabutylammonium iodide, tetramethylammonium chloride, tetramethylammonium iodide, tetraethylammonium iodide, tetraethylammonium chloride, tetraethylammonium bromide, Aliquat 336, alkyltrimethyl ammonium bromide, 18-crown-6, 15-crown-5, dibenzo-18-crown-6, tetraphenylphosphonium bromide, tri-tert-butylphosphonium tetrafluoroborate, (ethyl) triphenylphosphonium bromide, and tetrabutylphosponium bromide. Other phase-transfer catalysts that do not fall within the description above, such as bis(triphenylphophoranylidene)ammonium chloride, may also be suitable for this reaction. Preferred catalysts are lower tetraalkylammonium halides ($C_1$-$C_4$ alkyl), such as tetrabutylammonium halides, tetraalkyl ammonium iodides such as tetramethyl ammonium iodide, and preferably tetrabutyl ammonium iodide.

The base used in the alkylation step is generally a carbonate, phosphate, or hydroxide of an alkali metal, including alkali metal hydrogen carbonates, hydrogen phosphates, and dihydrogen phosphates. These include, but are not limited to, $K_2CO_3$, $Na_2CO_3$, $Cs_2CO_3$, $K_3PO_4$, $K_2HPO_4$, KOH, and NaOH. Typically, excess base is used. A large excess of base is not generally required in the process disclosed herein. About 1-4 equivalents of base relative to the biaryl chloride reactant is generally sufficient. In many embodiments, the amount of base is about 1-3 equivalents, and in preferred embodiments about 2 equivalents. In the process disclosed in WO 2007/005572, the bases that were used are very strong bases, such as sodium hexamethydisilazide (NaHMDS), resulting in some epimerization at the stereogenic centers. The amount of epimerization with NaHMDS is less than 2% using the procedure of WO2007/005572, but the amount of epimerization is very sensitive to small variations in the amount of base. The bases described above for use with the phase transfer catalysts are mild compared with NaHMDS. The amount of epimerization is less than 1% or is non-detectable for the reactions carried out with the phase transfer catalysts and the bases described above.

Typical solvents that may be used in the alkylation reaction include, but are not limited to, dimethyl sulfoxide (DMSO), N,N-dimethylformamide (DMF), acetonitrile, N,N-dimethylacetamide (DMAC), 1,3-dimethyl-2-imidazolidinone (DMI), N-methyl-2-pyrrolidone (NMP), sulfolane, isopropyl acetate, tetrahydrofuran, 2-methyltetrahydrofuran, and combinations thereof. Preferred solvents include DMF, acetonitrile, and DMSO. DMF is a highly preferred solvent. Acetonitrile is a highly preferred solvent. DMSO is a highly preferred solvent.

The temperature of the alkylation reaction is between about 50 and 100° C., preferably between about 50 and 80° C., and is about 60° C. in preferred embodiments.

The first three steps of the process were designed to eliminate or greatly reduce the amount of the impurity shown below (the "ethyl impurity"), which is difficult to remove and generates additional impurities by reacting in subsequent steps of the process:

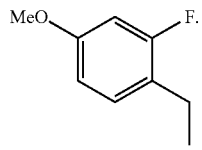

While not being bound by a particular reaction mechanism, it is believed that the "ethyl impurity" could be produced by hydrogenation of a byproduct that occurs during the first step of the process (the Grignard reaction) under the hydrogenation conditions of the previously published process. Based on NMR data, the impurity is believed to be the hemiketal shown below:

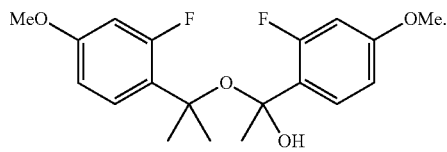 [SMILES: COc1ccc(C(C)(C)OC(C)(O)c2ccc(OC)cc2F)c(F)c1]

In the process described herein, the Pd catalyst, which is "poisoned" with diphenylsulfide, is believed to be less active and more selective in its activity so that it produces little or no ethyl impurity during the hydrogenation step. The acetophenone that is the starting material in the process is produced as a byproduct during the hydrogenation step using the poisoned Pd catalyst. Since the acetophenone impurity is not brominated under the conditions of the bromination step of this process, it is removed unchanged during subsequent steps of the process using the purification procedures that are already in place. The process steps described above reduce the amount of "ethyl impurity" so that there is little or no ethyl impurity in the product after step (2), which means that the ethyl impurity is at a level comparable to or less than what is attained with the corresponding process steps in WO 2007/005572 but without having to use the cerium salt that is used in WO 2007/005572.

The possible explanation above of why the amount of the ethyl impurity is diminished by the sequence of the two process steps and the structure of the proposed intermediate are believed to be correct and are provided for informational purposes only. The applicants do not wish to be bound to the accuracy of the explanation or the identity of the proposed intermediate.

In summary, the first two steps of the overall process are (1) the reaction of MeMgCl with the acetophenone starting material in the absence of a transition metal or lanthanide metal salt, such as $CeCl_3$, to yield a benzyl alcohol; and (2) the subsequent hydrogenation of the benzyl alcohol product using a palladium catalyst together with an organic sulfide to yield 2-fluoro-1-isopropyl-4-methoxybenzene which contains little or no ethyl impurity. In preferred embodiments, the organic sulfide is diphenyl sulfide. In preferred embodiments, the solvent for the first step is THF. In preferred embodiments, THF is the only solvent for the first step.

Definitions

The technical terms and abbreviations used throughout this application, in the Scheme, and in the examples, are generally well known to chemists who work in the area of organic chemistry in general and particularly process chemistry. Many of the terms and abbreviations are defined below, but other terms and abbreviations that may not have been defined herein are readily found and defined on internet search engines, such as Google.

"DIPEA" is diisopropylethylamine.

"DMF" is N,N-dimethyformamide.

"DMAC" is N,N-dimethylacetamide.

"DMI" is 1,3-Dimethyl-2-imidazolidinone

"DMSO" is dimethylsulfoxide.

"Halogen" includes fluorine, chlorine, bromine and iodine.

"IPAC" is isopropyl acetate.

"IPA" is isopropyl alcohol.

"iPr" is isopropyl.

"Me" represents methyl.

"MeCN" is acetonitrile.

"$(4\text{-MeOC}_6\text{H}_4)_3\text{P}$" is tris(4-methoxyphenyl) phosphine.

"NaHMDS" is sodium hexamethydisilazide.

"NMP" is N-methylpyrrolidone.

"$PCy_3$ is tricyclohexyl phosphine.

Solka-Floc® is a commercial powdered cellulose which can be a filter aid.

"TBAI" is tetrabutylammonium iodide.

"THF" is tetrahydrofuran.

"TFA" is trifluoroacetic acid.

"TMEDA" is tetramethylethylenediamine.

Step 1. 2-(2-Fluoro-4-methoxyphenyl)propan-2-ol

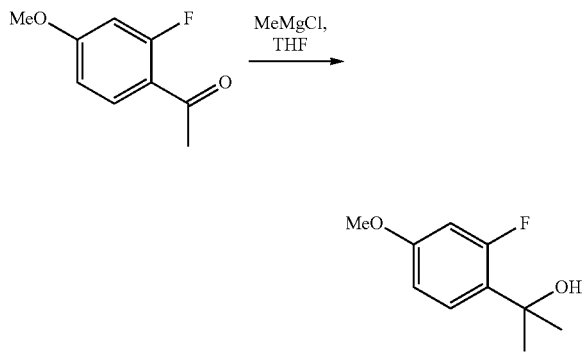

A solution of 2-fluoro-4-methoxyacetophenone (78.1 g, 460 mmol) in tetrahydrofuran (58.6 ml) was added to 3M methylmagnesium chloride solution in THF (199 ml, 598 mmol) at 20 to 35° C. under a nitrogen atmosphere over 30 min without cooling. Additional THF (19.53 ml) was used to rinse all starting material into the vessel. After complete addition, the mixture was stirred at 30° C. for 10 min., then was quenched into acetic acid (52.6 ml, 920 mmol) and water (273 ml) at 5-25° C. THF (20 ml) was used to rinse the vessel. Heptane (156 ml) was then added. The biphasic mixture was stirred at 20-25° C. for 30 min, and then the organic layer was separated. The organic layer was assayed and was found to contain 83.0 g of the desired product, which corresponds to 98% yield. The organic layer was concentrated under vacuum to remove THF, then was flushed with IPAC (200 ml), and the volume was increased to 500 ml by addition of more IPAC. This was used directly in the next step.

Step 2. 2-Fluoro-1-isopropyl-4-methoxybenzene

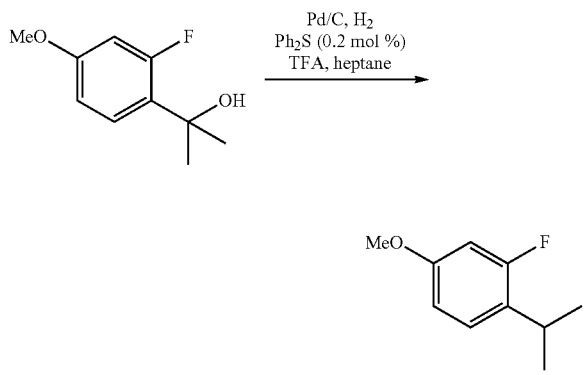

The solution of 2-(2-fluoro-4-methoxyphenyl)propan-2-ol in IPAC (500 ml, 451 mmol) and diphenyl sulfide (0.151 ml, 0.901 mmol) were combined in a hydrogenation shaker. The reaction mixture was purged with nitrogen/vacuum cycles, and 5% palladium on carbon (7.67 g, 1.802 mmol) was added, followed by TFA (17.36 ml, 225 mmol). Hydrogenation was conducted at 60° C. under 50 psig pressures for 12 h. The catalyst was removed by filtration through a 1 inch plug of Solka-Floc® powdered cellulose and rinsed with IPAC (49.8 ml). The filtrate was assayed and was found to contain 76 g of the desired product, which corresponds to a quantitative yield.

Step 3. 2-Bromo-4-isopropyl-5-fluoroanisole

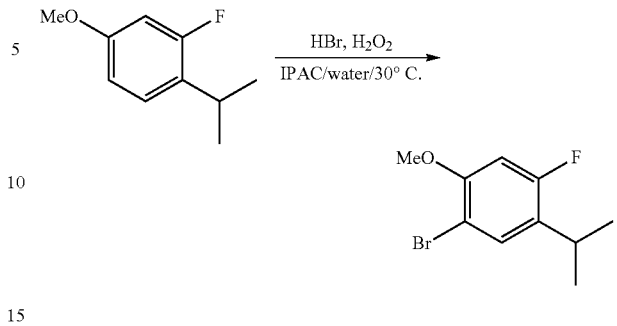

The crude 3-fluoro-4-isopropylanisole solution from the previous step (100 ml, 0.82 M, 82 mmol) was stirred at 20° C. in the dark. Aqueous 48 wt % HBr (16.6 g, 98.5 mmol) and aqueous 35 wt % hydrogen peroxide (14.0 g, 144 mmol) were added concomitantly over 40 min. The reaction mixture was maintained at 25-30° C. during the addition. The mixture was stirred at 30° C. for 3 h and then was cooled to 5° C. Sodium sulfite (4.2 g) was added in portions over 30 min while maintaining the quench temperature at <20° C. The aqueous layer was removed, and the organic layer was washed with 2 M $KHCO_3$ (20 ml), concentrated, and flushed with heptane (50 ml) at 30-40° C. under reduced pressure to afford 2-bromo-4-isopropyl-5-fluoroanisole as a pale yellow liquid in 98% yield.

Step 4a. 4-Fluoro-5-isopropyl-2-methoxyphenylboronic acid

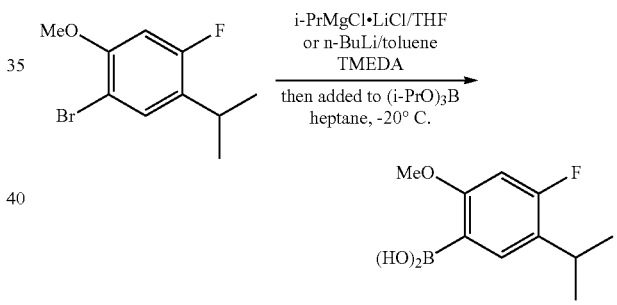

A mixture of 2-bromo-4-isopropyl-5-fluoroanisole (85.4 wt %, 8.71 g, 30.1 mmol) and TMEDA (6.1 ml, 40.6 mmol) was placed in an oven-dried 100 ml 3 necked flask equipped with a magnetic stirrer and reflux condenser. The mixture was placed under an inert atmosphere by applying a vacuum/nitrogen cycle three times, and then i-PrMgCl.LiCl in THF (1.07 M, 38.0 ml, 40.6 mmol) was added slowly. The resulting brownish grey solution was warmed to 40° C. and was aged at that temperature for 3 hours, after which it was cooled to room temperature.

In a separate oven-dried 250 ml, 3 necked flask equipped with a mechanical stirrer was placed isopropyl borate (11.2 ml, 48.2 mmol) solution in heptane (22 ml), and the mixture was cooled to −20° C. To this was added the Grignard solution, while maintaining the internal temperature at or below −20° C. over 30 min. After the addition was complete, the mixture was aged 30 min at −20° C., then 3 M $H_2SO_4$ (45 ml) was added, allowing the internal temperature to rise to ca. 20° C.

The resulting biphasic mixture was transferred to a separatory funnel with the aid of THF/heptane (1/1, 7 ml), and the aqueous layer was removed. The organic layer was extracted with 2 M KOH (30 ml) followed by 2 M KOH (15 ml). The combined KOH extracts were transferred to a 250 ml 3-necked flask equipped with a mechanical stirrer with the aid of IPA (8ml). The clear, pale yellow solution was cooled to 10° C., and 3 M $H_2SO_4$ (15 ml) was added slowly over 30 min. The resulting thick slurry was aged for an hour at 10° C., then was filtered to collect the solid. The solid was washed with water (45 ml), 5% $NaHCO_3$ (45 ml), and finally with water (90 ml). The white crystalline solid thus obtained was dried under vacuum with a nitrogen sweep overnight to afford 5.57 g, 98.26 wt % (Yield=86%, corrected for purity).

Step 4b. 4-Fluoro-5-isopropyl-2-methoxyphenylboronic acid

A solution of 2-bromo-4-isopropyl-5-fluoroanisole (88 wt % in toluene, 10.44 g, 37.2 mmol) in anhydrous toluene was cooled to −10° C. under $N_2$ atmosphere, and 2.5 M, n-butyllithium solution in hexanes (16.36 ml, 40.69 mmol) was added slowly. After stirring at the same temperature for 10 minutes, the resulting solution was transferred to a cooled solution of triisopropyl borate (14.53 ml, 61.3 mmol) and TMEDA (2.80 ml, 18.59 mmol) in toluene slowly at −20° C. After stirring for 30 minutes, the reaction mixture was quenched with 3M $H_2SO_4$ (45 ml), and the resulting mixture was worked up as described in Step 4a to provide the title compound in 83% yield (6.62 g, 98.5 wt %).

Step 5a. Palladium Catalyzed Suzuki Coupling—AllylPdCl Dimer Catalyst

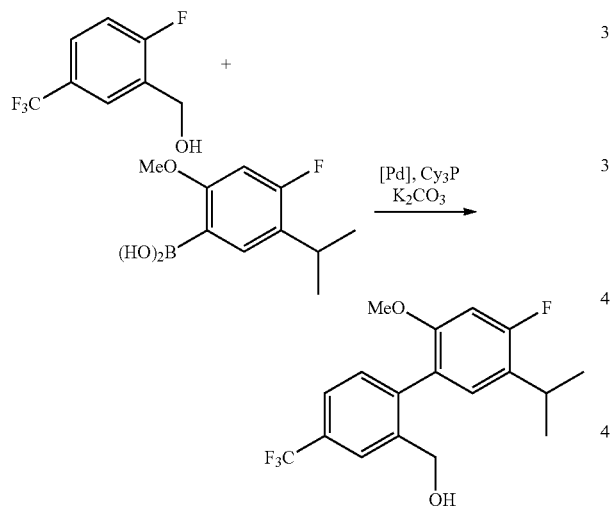

In a 250 ml flask equipped with a reflux condenser was placed 2-chloro-5-(trifluoromethyl)benzyl alcohol (10 g; 47.5 mmol), 4-fluoro-5-isopropyl-2-methoxyphenylboronic acid (10.81 g; 95 wt % purity, 48.4 mmol), acetonitrile (80 ml) and 3 M $K_2CO_3$ (42.7 ml, 128 mmol). The resulting biphasic solution was sparged with nitrogen for several minutes. [AllylPdCl]$_2$ (0.043 g, 0.119 mmol) and PCy$_3$.HBF$_4$ (0.087 g, 0.237 mmol) were added under nitrogen flow, and the reaction mixture was warmed to 70° C. until HPLC showed the reaction was complete.

The reaction mixture was then cooled to room temperature and the phases were separated. The organic layer was washed with 10% NaCl solution (50 ml). After phase separation, Darco® KB-G activated carbon (2.0 g) was added to the organic layer, and the mixture was stirred for 1 hr at room temperature. The mixture was then filtered through a pad of Solka-Floc®. The filtrate was assayed and was found to contain 15.5 g of product (95% yield). The filtrate was azeotropically dried with acetonitrile and concentrated to an oil under vacuum. The crude product was used in the next step without further treatment.

Step 5b. Palladium Catalyzed Suzuki Coupling—Aminobiphenyl-PCy$_3$ Precatalyst

In a 50 ml flask equipped with a reflux condenser was placed 3 M $K_2CO_3$ (12.82 ml, 38.5 mmol), 4-fluoro-5-isopropyl-2-methoxyphenylboronic acid (3.24 g, 95 wt %, 14.53 mmol), 2-chloro-5-(trifluoromethyl)benzyl alcohol (3 g, 14.25 mmol), isopropyl alcohol (9 ml) and IPAC (9 ml). The resulting biphasic solution was sparged with nitrogen for approximately 45 min after which the (2'-aminobiphenyl-2-yl)palladium(II) chloride-tricyclohexyl phosphine precatalyst (0.042 g, 0.071 mmol) was charged under positive nitrogen flow. The reaction was then aged at 75° C. for approximately 3 hours or until the reaction was complete. The reaction mixture was then cooled to room temperature, diluted with isopropyl acetate, and the layers were separated. The organic layer was assayed and found to contain 4.78 g of the desired coupling product, which corresponds to 98% yield. The resulting organic layer was washed with water. To the organic layer was added Darco® KB-BG (0.75 g), and the mixture was stirred at room temperature for 1 hour, after which it was filtered through Solka-Floc®. The filtrate was concentrated and used without further purification in the next (chlorination) step.

Step 5c. Nickel Catalyzed Suzuki Coupling

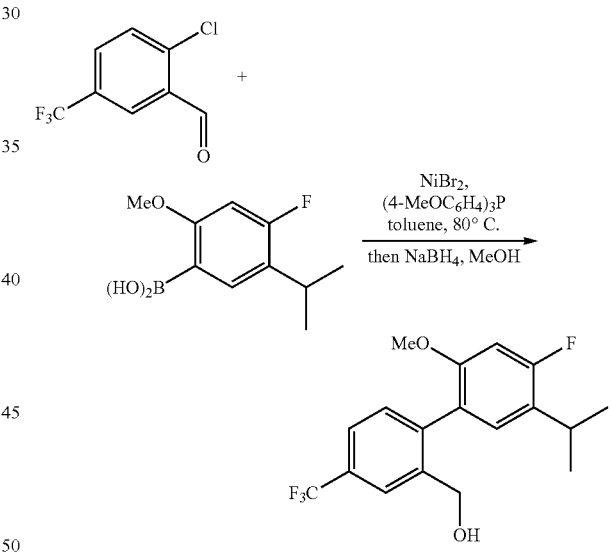

A mixture of nickel bromide (10.3 mg, 0.047 mmol) and tris(4-methoxyphenyl) phosphine (33 mg, 0.094 mmol) was placed in an 8 ml vial, and toluene was added (1 ml). The resulting slurry was stirred under nitrogen in a glovebox for 2.5 hours. The resulting dark green mixture was transferred to a mixture of 2-chloro-5-(trifluoromethyl)benzaldehyde (1.0 g, 4.7 mmol), 4-fluoro-5-isopropyl-2-methoxyphenylboronic acid (1.07 g, 4.8 mmol), potassium phosphate (1.6 g, 7.5 mmol), and toluene (9 ml). The resulting mixture was stirred at 80° C. for 15 hours, and was then cooled to room temperature. To this was added sodium borohydride (0.18 g, 4.7 mmol) and methanol (2 ml). After the reaction was complete as judged by HPLC analysis, the reaction mixture was acidified by adding hydrochloric acid. The organic layer was assayed and was found to contain 1.33 g of the desired product, which corresponded to an 83% yield.

Step 6. 2'-(Chloromethyl)-4-fluoro-5-isopropyl-2-methoxy-4'-(trifluoromethyl)biphenyl

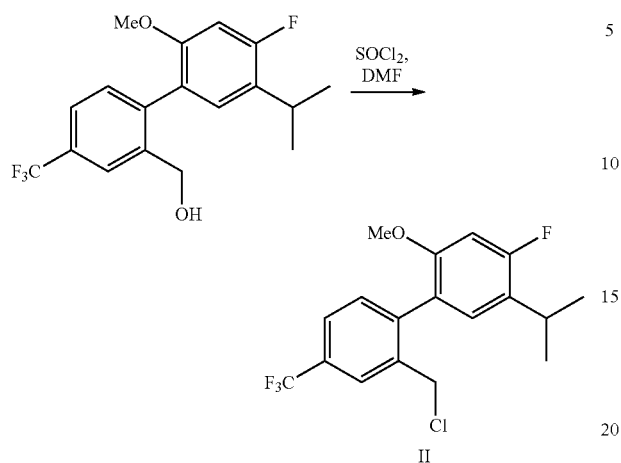

A mixture of biaryl alcohol (5.23 g, 15.28 mmol) and DMF (26.2 ml) was cooled to <10° C., and thionyl chloride (1.45 ml, 19.86 mmol) was added slowly over 1 hour. The resulting reaction mixture was aged at 10-15° C. until the reaction was completed. To the mixture was added water (5.23 ml), and the resulting slurry was stirred for an hour at 10° C. Additional water (5.23 ml) was added slowly over 1 hour at 10° C., and the slurry was allowed to warm to room temperature. The solid was collected by filtration, washed with 1:1 DMF:water solution (26 ml) followed by water (52 ml), and dried under vacuum to afford 5.36 g of solids; 99.6 wt % (5.33 g corrected for purity; 96.8%).

Step 7. (4S,5R)-5-(3,5-bis(trifluoromethyl)phenyl)-3-((4'-fluoro-5'-isopropyl-2'-methoxy-4-(trifluoromethyl)-[1,1'-biphenyl]-2-yl)methyl)-4-methyloxazolidin-2-one (anacetrapib)

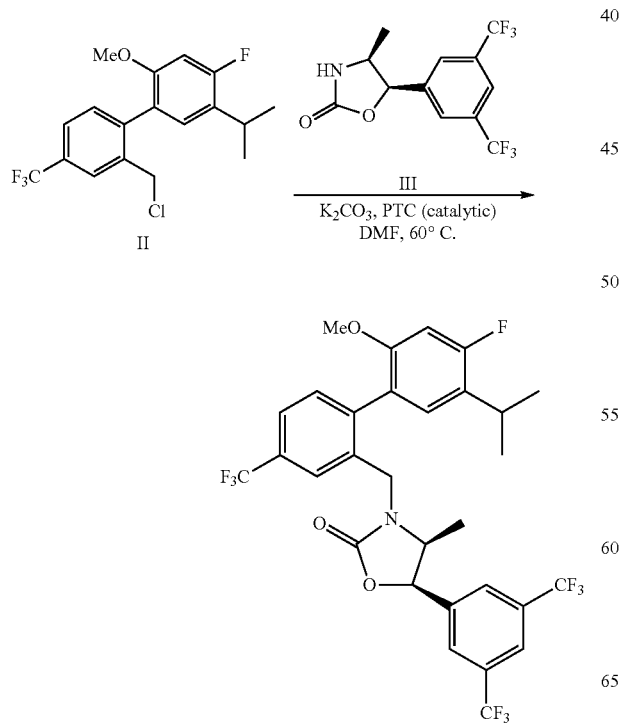

Oxazolidinone III (9.58 g, 30.6 mmol), biaryl chloride II (10.83 g, 30.0 mmol), tetrabutylammonium iodide (0.02 molar equivalents, based on the amount of biaryl chloride), K$_2$CO$_3$ (2 equivalents), and DMF (12 mL) were charged to a 100 mL flask, and the resulting slurry was stirred at 60° C. for 17 hours. Then n-heptane and water were added at the same temperature. The aqueous layer was removed, and the organic layer was washed with water. The product was crystallized by cooling the organic mixture. Isolated crystals were washed with heptane and dried to afford 17.60 g of the titled compound (27.6 mmol, 92%).

What is claimed is:
1. A process for synthesizing the compound of Formula I:

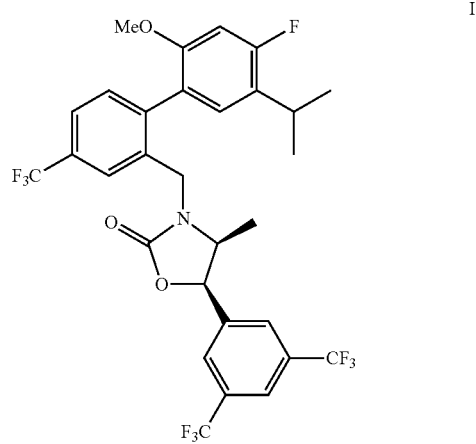 [SMILES: COc1cc(F)c(C(C)C)cc1-c1ccc(C(F)(F)F)cc1CN1C(=O)O[C@H](c2cc(C(F)(F)F)cc(C(F)(F)F)c2)[C@@H]1C]

comprising the step of combining the compounds of formula II and III

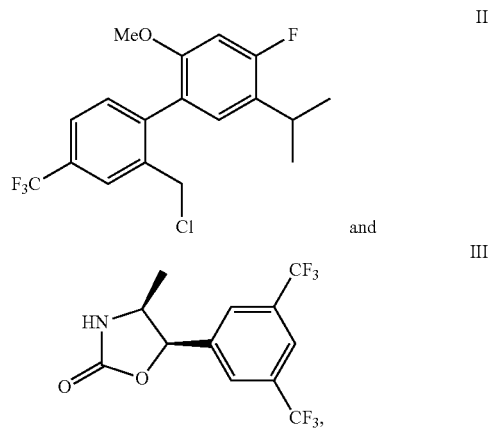

in the presence of a phase transfer catalyst and a base in a solvent, wherein the base is an alkali metal hydroxide, carbonate, hydrogen carbonate, phosphate, hydrogen phosphate, or dihydrogen phosphate.

2. The process of claim 1, wherein the phase transfer catalyst is a tetraalkylammonium halide, a crown ether, or a quaternary phosphonium halide.

3. The process of claim 2, wherein the solvent is dimethyl sulfoxide (DMSO), N,N-dimethylformamide (DMF), acetonitrile, N,N-dimethylacetamide (DMAC), 1,3-dimethyl-2-imidazolidinone (DMI), N-methyl-2-pyrrolidone (NMP), sulfolane, isopropyl acetate, tetrahydrofuran, or 2-methyltetrahydrofuran, or a combination thereof.

4. The process of claim 3, wherein the base is $K_2CO_3$, $Na_2CO_3$, $Cs_2CO_3$, $K_3PO_4$, $K_2HPO_4$, KOH, or NaOH.

5. The process of claim 4, wherein the catalyst is a tetraalkylammonium iodide.

6. The process of claim 5, wherein the solvent is DMF, acetonitrile, or DMSO.

7. The process of claim 6, wherein the catalyst is tetrabutylammonium iodide.

8. The process of claim 7, wherein the temperature of the reaction is 50-100° C.

9. The process of claim 8, wherein the solvent is DMF.

10. The process of claim 8, wherein the solvent is acetonitrile.

11. The process of claim 8, wherein the solvent is DMSO.

* * * * *

UNITED STATES PATENT AND TRADEMARK OFFICE
CERTIFICATE OF CORRECTION

PATENT NO. : 9,145,348 B2
APPLICATION NO. : 14/355105
DATED : September 29, 2015
INVENTOR(S) : Cheol K. Chung et al.

It is certified that error appears in the above-identified patent and that said Letters Patent is hereby corrected as shown below:

Title Page

Item (73) Assignee replace "Merck Sharpe & Dohme Corp., Rahway, NJ (US)" with --Merck Sharp & Dohme Corp., Rahway, NJ (US)--.

Signed and Sealed this
Fifth Day of July, 2016

Michelle K. Lee
*Director of the United States Patent and Trademark Office*